United States Patent [19]

Nagy et al.

[11] Patent Number: 5,186,723
[45] Date of Patent: Feb. 16, 1993

[54] PROCESS FOR THE PREPARATION AND USE OF ANTIDOTE-CARRYING MAIZE PLANT PARTS USEFUL FOR LOWERING THE CULTIVATED PLANT-DAMAGING EFFECT OF THIOLCARBAMATES AND CHLOROACETANILIDES

[75] Inventors: József Nagy; István Nagy; Károly Balogh; Erzsébet Mile; Gyula Tarpai; Katalin Sellei née Kulik; Károly Fodor, all of Miskolc; Mihály Kecskés, Budapest; Erzsébet Tóth née Juhász, Miskolc; Zsuzsanna Horváth née Pethó, Gödölló, all of Hungary

[73] Assignee: Eszakmagyarorszagi Vegyimuuek, Sajobabony, Hungary

[21] Appl. No.: 304,355

[22] Filed: Jan. 30, 1989

[51] Int. Cl.$^5$ .................. A01C 1/06; A01N 65/00
[52] U.S. Cl. ...................... 47/58; 424/93 U; 47/57.6
[58] Field of Search .............. 71/65, 100; 424/93, 424/93 U; 435/822; 47/58, 57.6

[56] References Cited

U.S. PATENT DOCUMENTS 4,517,008  5/1985  Strobel et al. ................ 71/77

OTHER PUBLICATIONS

Seuferer et al. (1979) Pesticide Biochemistry and Physiology 10:174–180.
Tam et al. (1988) J. Agric. Food Chem. 36:654–657.
Gressel et al. (1982) Easter School in Agricultural Science, proceedings, London, Butterworths, vol. 33, pp. 79–91.
O'Connell et al. (1988) Plant Physiol 86:359–363, Biosis Abstract May 1988.

Primary Examiner—Che S. Chereskin
Attorney, Agent, or Firm—Herbert Dubno; Jonathan Myers

[57] ABSTRACT

The invention relates to a process for the preparation and use of antidote-carrying maize plant parts which are useful for lowering the cultivated plant-damaging effect of thiolcarbamates and chloroacetanilides, which comprises treating native or artificially genmanipulated macroorganisms living in the soil or on the soil surface by the thiolcarbamate and chloroacetanilides compounds and using the living organisms thus made antidote-carrying for the treatment of field soils in a fresh state or after preservation by lyophilization or by application onto a carrier in their original state or after working up them by crushing, pulverisation, extraction or drying, before or simultaneously with or after the treatment with the herbicides, in any time until the germination of the cultivated plant, whereby the selectivity of thiolcarbamates of the formula (I) and chloroacetanilides against cultivated plants, preferably against the maize is increased.

3 Claims, No Drawings

PROCESS FOR THE PREPARATION AND USE OF ANTIDOTE-CARRYING MAIZE PLANT PARTS USEFUL FOR LOWERING THE CULTIVATED PLANT-DAMAGING EFFECT OF THIOLCARBAMATES AND CHLOROACETANILIDES

FIELD OF THE INVENTION

The invention relates to a process for the preparation and use of antidote-carrying micro- and which are useful for lowering the cultivated plant-damaging effect of thiolcarbamates of the formula (I),

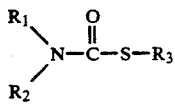

wherein
$R_1$ and $R_2$ are the same or different, and stand for $C_{1-6}$alkyl or $C_{3-6}$cycloalkyl group, or $R_1$ and $R_2$ together with the nitrogen atom, to which they are attached, form a hexamethylenimino group; and
$R_3$ means a $C_{1-5}$alkyl group, or chloroacetanilides of the formula (VIII),

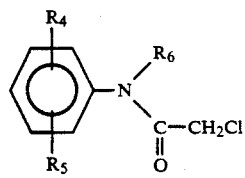

wherein
$R_4$ and $R_5$ are the same or different and stand for hydrogen or $C_{1-5}$alkyl group; and
$R_6$ means a $C_{1-5}$alkyl, $C_{2-5}$alkenyl, $(C_{1-3}$alkoxy$)$-$(C_{1-3}$alkyl$)$ or pyrazolyl-$(C_{1-3}$alkyl$)$ group.

BACKGROUND OF THE INVENTION

It is commonly known from the practice of plant protection that thiolcarbamates of the formula (I), particularly EPTC [S-ethyl-N,N-di(n-propyl)thiolcarbamate], butylate [S-ethyl-N,N-di(isobutyl)thiolcarbamate], vernolate [S-propyl-N,N-di(n-propyl)thiolcarbamate], ethiolate (S-ethyl-N,N-diethylthiolcarbamate), cycloate (S-ethyl-N-ethyl-N-cyclohexylthiolcarbamate) and molinate (S-ethyl-N,N-hexamethylenethiolcarbamate), as well as chloroacetanilides of the general formula (VIII), particularly alachlor (2-chloro-2',6'-diethyl-N-methoxymethylacetanilide), acetochlor (2-chloro-2'-ethyl-6'-methyl-N-ethoxymethylacetanilide) and propachlor (2-chloro-N-isopropylacetanilide) are very effective herbicides.

However, a common drawback of both classes of these herbicidally active agents consists in their relatively low selectivity against some cultivated plants, mainly maize.

When used in the usual herbicidally active doses, EPTC, vernolate and acetochlor may induce significant phytotoxic symptoms. About twenty five years ago, Hoffmann recognized that there are compounds, such as 1,8-naphthalic acid anhydride derivatives which are able to diminish the phytotoxic effect. Since that time, research has been undertaken to find synthetic compounds antagonizing the cultivated planting-damaging effect of herbicides.

The antidotal action of some compound classes have been disclosed in several Hungarian patent specifications mentioned hereinafter.

No. 165,736: The thiolcarbamate-antidoting action of dichloroacetamide derivatives, e.g. N,N-diallyl-2,2-dichloroacetamide (code No. R-25 788);

No. 168,977: Oxazolidine and thiazolidine type antidotes, particularly useful against thiolcarbamates;

No. 170,214: Thiazolidine sulfoxide and sulfone type antidotes, useful against thiolcarbamates and chloroacetanilides;

No. 173,775: Sulfide type antidotes, useful against thiolcarbamates;

No. 176,867: Oxazolidine derivatives useful for antidoting thiolcarbamates;

No. 179,643: N-Benzoylsulfonylcarbamate compounds, useful for antidoting thiolcarbamates;

No. 180,069: N-Benzoylsulfonylthiolcarbamate compounds, useful for antidoting thiolcarbamates; and No. 180,068: 2,3-Dibromopropionamide derivatives, useful as antidotes against thiolcarbamates;

Nos. 174,487, 176,784, 180,422, 181,621, 183,997, 185,400 and 188,135: Substituted acetamide type antidotes, useful against thiolcarbamates and chloroacetanilides.

Dicarboxylic acid derivatives with different chemical structures antidoting thiolcarbamates and/or chloroacetanilides have been described in the Hungarian patent specifications Nos. 176,669, 176,796, 178,892 and 178,895; the antidoting effect of naphthalenecarboxylic acid derivatives has been described in the Hungarian patent specifications Nos. 178,883, 179,092 and 179,093.

A result in the increase of selectivity of thiolcarbamates has been described in a paper of J. E. Casida et al. "Thiocarbamate sulfoxide herbicides" in 1974. The main point of this paper is that the sulfoxide of EPTC, which is a decomposition product of EPTC, shows a useful herbicidal action but is not harmful to the maize. However, the recognition of these authors distended only to the use of the EPTC-sulfoxide in itself which cannot be used in practical plant protection because of its other disadvantageous properties (e.g. it cannot be used in all types of soils).

In spite of the results of research described in a large number of patent specifications, successful to find a compound that is able to provide general protection against the harmful effects of various herbicides, has not been found heretofore by the fact a fact supported also that the research directed to clarify the antidoting action were unable to develop a uniform standpoint for deciding the biochemical processes occurring in the case of adding antidotes, or for defining the influence of these antidotes on the processes induced by the herbicides in the cultivated plants.

DESCRIPTION OF THE INVENTION

In the course of our research directed to decrease in the cultivated plant-damaging effect of hebicides of the thiolcarbamate type of the formula (I) and chloroacetanilides of the formula (VIII), it has been found that the compounds of the formulae (II) to (VII)

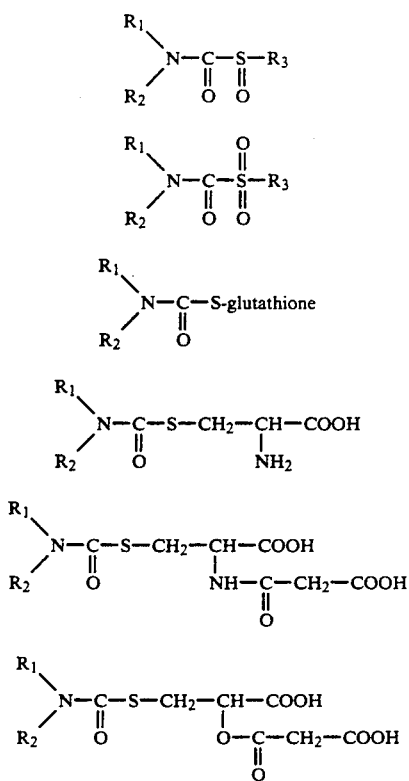

wherein in the compounds of the formulae (I) to (VIII)
$R_1$ and $R_2$ are the same or different, and stand for $C_{1-6}$alkyl or $C_{3-6}$cycloalkyl group, or $R_1$ and $R_2$ together with the nitrogen atom form a hexamethylenimino group;

$R_3$ means a $C_{1-5}$alkyl group;

$R_4$ and $R_5$ are the same or different, and represent hydrogen or a $C_{1-5}$alkyl group; and $R_6$ stands for a $C_{1-5}$alkyl, $C_{2-5}$alkenyl, $(C_{1-3}$alkoxy)-$(C_{1-3}$alkyl) or pyrazolyl-$(C_{1-3}$alkyl) group formed in the soil or in micro- or macroorganisms pretreated with thiolcarbamates of the formula (I), or their acylated or esterified derivatives can successfully be used for protection from the phytotoxicity of the herbicides of both kinds when the compounds of the formulae (I) to (VII) are applied onto the soil before or simultaneously with or after the treatment with the herbicidally active agents.

Thus, the present invention relates to processes wherein native or artifically genmanipulated micro- or macroorganisms living in the soil or on the soil surface, or their organ or cell cultures or cell components are treated with compounds of the formulae (I) to (VII), preferably with EPTC.

In the course of the treating process, the decomposition products formed from the compounds of the formulae (I) to (VII), which may be preferably one of the compounds of the formulae (II) to (VII) or their mixture or an acylated or esterified derivative thereof, show a herbicide-antidoting action and are bound to the micro- or macroorganisms whereby antidote-carrying living organisms are obtained as a final result.

The present invention relates also to the use of the antidote-carrying micro- and macroorganisms, obtained by using the above processes, for lowering the cultivated plant-damaging effect of thiolcarbamates of formula (I) and chloroacetanilides of formula (VIII).

These micro- and macroorganisms are used either in a fresh state or after preservation by lyophilization or by applying them on a carrier, in their original form or after working them up by crushing, pulverisation, extraction, drying or in an other way, before or simultaneously with (in the form of a manufactured combination or tank mixture) or after the treatment with the herbicides, in any time until the germination of the cultivated plant for treating the field soils, whereby the selectivity of the herbicidally active compounds of the formulae (I) and (VIII) against cultivated plants, preferably to maize is increased.

SPECIFIC EXAMPLES

The invention is illustrated in detail by the following non-limiting Examples.

EXAMPLE 1

Investigation of the soil, pretreated with EPTC belonging to the herbicides of the general formula (I), as a carrier of the antidoting metabolic products of microbial origin A field soil having a pH-KCl value of 5.7, a heaviness of 46 AK and containing 0.03% of total salts, 1.9% of humus, 14.8 ppm of $NO_3+NO_2$, 735 ppm of $P_2O_5$, 853 ppm of $K_2O$, 246 ppm of Mg, 60 ppm of Na, 2.1 ppm of Zn, 3.2 ppm of Cu and 151 ppm of Mn was pretreated with a 8 l/ha dose of Witox 72 EC containing 72% of active agent as a formulation of the EPTC herbicide, or with a 8 l/ha dose of Alirox 80 EC containing 72% of EPTC and 8% of AD-67 [N-(2,2-dichloroacetyl)-1-oxa-4-azabicyclo[4,5]decane] as antidote.

600 g of this soil each were weighed in cultivating bottles and 10 grains of various species of hybrid maize as well as 20 grains of sorghum each as weed were sowed therein.

On the day 11 after sowing, while the plants were cultivated under HgMIF 400/D daylight lamps with an illumination period of 16 hours and daily sprinkled up to the water capacity of the soil, the green mass of the plants as well as the shoot length of the maize were measured and the exterior of the maize was evaluated by the following bonitation scale:

4: strong deformation, torsion
3: medium deformation, torsion
2: mild phytotoxicity
1: intact, healthy plant.

Thereafter, on the day 14 after the first sowing, the plants were again sowed into the cultivating bottles and the soil was treated with a 8 l/ha or 20 l/ha dose, respectively, of Witox 72 EC containing 72% of EPTC.

On the day 11 after the second sowing, the green mass of the plants and the shoot length of the maize were measured.

It can be stated from the data of Table I that the various species of hybrid maize, sowed in the soil pretreated with EPTC or with EPTC antidoted by AD-67, respectively, tolerated well both the 8 l/ha and 20 l/ha doses of EPTC whereas the sorghum sown as a weed was destroyed.

TABLE I

Development of the shoot length, green mass and exterior of hybrid maizes as well as change in the green mass of sorghum under the effect of treatments with EPTC

|  | Untreated control | Dose of EPTC | |
| --- | --- | --- | --- |
|  |  | 8 l/ha | 20 l/ha |
| Shoot length of maize (cm/plant) | | | |
| 1st sowing | 21 | 8 | — |
| 2nd sowing | 19 | 19 | 19 |
| Green mass of maize (g/plant) | | | |
| 1st sowing | 0,56 | 0,49 | — |
| 2nd sowing | 0,5 | 0,59 | 0,63 |
| Bonitation (maize) | | | |
| 1st sowing | 2,0 | 1,2 | — |
| 2nd sowing | 2,0 | 2,0 | 2,0 |
| Green mass of sorghum (g/bottle) | | | |
| 1st sowing | 0,15 | 0 | — |
| 2nd sowing | 0,14 | 0 | 0 |

EXAMPLE 2

An experiment was carried out in laboratory cultivating bottles for investigating the synergistic, antagonistic action exerted by different thiolcarbamate type herbicides and antidote-carrying bacteria (NI-86/21 EPTC 250 bacterial suspension) on each other.

1. Materials, Equipments and Methods 1.1 Preparation of the NI-86/21 Bacterial Suspension A pure strain culture of the EPTC-decomposing NI-86/21 bacteria isolated from the soil was inoculated to 5 ml of slant Nutrient medium containing the following components:

| Meat extract | 1 g |
| --- | --- |
| Yeast | 2 g |
| Pepton | 5 g |
| NaCl | 5 g |
| Agar | 20 g |
| Distilled water | 1000 ml |
| pH | 7.4 |

In the following a culture was used which was older than 3 to 4 days but younger than 120 days.

Subsequently, the bacteria propagated in the glass tube were washed into 10 ml of sterilized distilled water. Thus, the suspension contained about $10^9$ bacteria in 1 ml each.

200 ml of physiological nutrient salt solution each were poured in 500 ml Erlenmeyer bottles. The composition of the nutrient salt solution as calculated for 1000 ml was as follows:

| $NH_4NO_3$ | 0.5 g |
| --- | --- |
| $KH_2PO_4$ | 0.4 g |
| $K_2HPO_4$ | 1.6 g |
| NaCl | 0.1 g |
| $MgSO_4.2H_2O$ | 0.2 g |
| $CaCl_2.2H_2O$ | 0.5 mg |
| $CuSO_4.5H_2O$ | 0.5 mg |
| $FeSO_4.7H_2O$ | 0.5 mg |
| $ZnCl_2$ | 0.5 mg |

The EPTC active ingredient was weighed into this solution in such a way that a concentration of 250 ppm was obtained. Then, 2 ml of this bacterial suspension each were mixed into the bottles which were then shaken on a shaking apparatus for 24 hours to obtain the antidote-carrying bacteria.

Further on, the selectivity of the herbicides (EPTC, butylate, vernolate, molinate) drawn into the experiments was examined in themselves and, on the other hand, in their combinations formed with 10 ml of the NI-86/21 EPTC 250 antidote-carrying bacterial suspension according to the treatments.

EXPERIMENT IN CULTIVATING BOTTLE

PVC foil-lined plastic bottles with a surface of 0.8 $dm^2$ were used, which were suitable to receive 800 g of soil each. First, 400 g of air-dry field soil each with a humus content of 1.95%, pH value of 5.7 and heaviness (according to Arany) of 46 were weighed into the bottles. Thereon 10 grains of Pioneer 3707 hybrid maize each, 20 grains of the cultivated "Alföldi 1" type sorghum each and 0.5 g of red millet each were sown. The sowing was covered by 100 g of soil each, then EPTC, vernolate and molinate as active ingredients were applied in a dose of 6 l/ha and butylate as active ingredient in a dose of 24 l/ha as manufactured compositions of EMV (Chemical Works of North-Hungary). The soil surface treated was covered by 100 g of soil each and then 10 ml of NI-86/21 EPTC 250 biopreparation each were applied onto the soil surface according to the treatment list given below.

List of treatments:

0 Untreated control
1 EPTC 6 l/ha
2 EPTC 6 l/ha + NI-86/21 EPTC 250 10 ml
3 Butylate 24 l/ha
4 Butylate 24 l/ha + NI-86/21 EPTC 250 10 ml
5 Vernolate 6 l/ha
6 Vernolate 6 l/ha + NI-86/21 EPTC 250 10 ml
7 Molinate 6 l/ha
8 Molinate 6 l/ha + NI-86/21 EPTC 250 10 ml

RESULTS OF THE CULTIVATING BOTTLE EXPERIMENT

The results of the cultivating bottle experiment are shown in the Tables II, III and IV.

It can be seen from Table II that the shoot length of the untreated control maize amounted to 22 cm. On using EPTC, vernolate or molinate in a dose of 6 l/ha or butylate in a dose of 24 l/ha in themselves, the shoot lengths were significantly diminished (to 9, 11, 13 or 12 cm, respectively). On the contrary, when 10 ml of NI-86/21 EPTC 250 biopreparation each were added to the herbicides mentioned above, then the shoot length-decreasing effect of EPTC, butylate and vernolate was abolished (21, 23 and 21 cm, respectively) whereas the phytotoxicity of molinate remained unchanged (17 cm).

The data illustrated in Table III relating the change in the green mass of maize showd a picture similar to that of the shoot length.

The maize was completely protected from the damaging effect of the herbicidally active EPTC, butylate and vernolate by using the NI-86/21 EPTC 250 suspension in a dose of 10 ml/cultivating bottle.

This fact is illustrated by Table IV, too from which the excellent antidoting action of this biopreparation can be seen on the basis of exterior of the maize.

The red millet and the sorghum sowed as weeds were destroyed by all treatments, i.e. these plants were not protected by the NI-86/21 EPTC 250 biopreparation.

TABLE II

Lowering of the phytotoxic effect induced on the maize shoot by EPTC, butylate, vernolate and molinate herbicides by the NI-86/21 EPTC 250 biopreparation

| Herbicide | Dose l/ha | Shoot length of maize (cm/plant) — | NI-86/21 EPTC 250 biopreparation |
|---|---|---|---|
| EPTC | 6 | 9 | 21 |
| Butylate | 24 | 12 | 23 |
| Vernolate | 6 | 11 | 21 |
| Molinate | 6 | 13 | 17 |

Shoot length of the untreated control maize was 22 cm.

TABLE III

Action on the maize green mass of EPTC, butylate, vernolate and molinate herbicides and their combinations with the NI-86-21 EPTC 250 biopreparation, respectively

| Herbicide | Dose l/ha | Green mass of maize ($10^{-2}$ g/plant) — | Ni-86/21 EPTC 250 biopreparation |
|---|---|---|---|
| EPTC | 6 | 51 | 86 |
| Butylate | 24 | 60 | 83 |
| Vernolate | 6 | 54 | 88 |
| Molinate | 6 | 57 | 64 |

The green mass of the untreated control maize amounted to $82 \times 10^{-2}$ g/plant.

TABLE IV

Action on the maize exterior of EPTC, butylate, vernolate and molinate herbicides and their combinations with the NI-86-21 EPTC 250 biopreparation, respectively

| Herbicide | Dose l/ha | Exterior of the maize (%) — | NI-86/21 EPTC 250 biopreparation |
|---|---|---|---|
| EPTC | 6 | 55 | 100 |
| Butylate | 24 | 61 | 100 |
| Vernolate | 6 | 63 | 100 |
| Molinate | 6 | 58 | 61 |

The exterior of the untreated control maize was taken as 100%.
Bonitation scale
100%: intact maize with normal development
99 to 87%: mild phytotoxicity, deformation of the shoot
86 to 75%: medium deformation of the shoot, torsion
75 to 51%: strong deformation of the shoot, destruction
50%: the maize was destroyed, remained in the shoot capsule.

EXAMPLE 3

The action on the EPTC selectivity of various amounts of the antidote-carrying NI-86/21 EPTC 250 bacterial suspension, prepared as described in Example 2, was investigated.

In this experiment, PVC foil-lined plastic cultivating bottles with a surface of 0.8 dm² were used, which were useful for receiving 800 g of air-dry soil each. First, 400 g of soil each were weighed into the bottles.

The upper field soil had a medium heaviness, a humus content of 1.95% and a pH value of 5.7. 10 grains of Pioneer 3707 hybrid maize each as test plant, as well as 20 grains of sorghum and 0.5 g of millet each were sown. The sowing was covered by 100 g of soil each, whereupon the treatments with thiolcarbamates and with NI-86/21 EPTC 250 biopreparations, respectively, were carried out as follows.

| Treatments: | |
|---|---|
| 0 Untreated control | |
| 1 EPTC 6 l/ha | |
| 2 EPTC 6 l/ha + NI-86/21 EPTC 250 | 1000 l/ha |
| 3 EPTC 6 l/ha + Ni-86/21 EPTC 250 | 5000 l/ha |
| 4 EPTC 6 l/ha + NI-86/21 EPTC 250 | 10000 l/ha |
| 5 EPTC 6 l/ha + NI-86/21 EPTC 250 | 20000 l/ha |

The soil surface treated was repeatedly covered by 100 g of soil each.

The experiment was evaluated on the day 10 after the treatment, when the shoot length and green mass of the maize as well as the green mass of the sorghum and millet were measured.

The advantages of the combinations containing EPTC together with NI-86/21 EPTC 250 are summarized in Table V.

TABLE V

Action of the NI-86/21 EPTC 250 biopreparation on the phytotoxicity of EPTC in a maize culture (data are given as percentage of the untreated control)

| | Maize | | Sorghum | Millet |
|---|---|---|---|---|
| Treatment | Green mass % | Shoot length % | Green mass % | Green mass % |
| 1 EPTC 6 l/ha | 74 | 41 | 0 | 0 |
| 2 EPTC 6 l/ha + NI-86/21 EPTC 250 1000 l/ha | 117 | 115 | 0 | 0 |
| 3 EPTC 6 l/ha + NI-86/21 EPTC 250 5000 l/ha | 113 | 112 | 0 | 0 |
| 4 EPTC 6 l/ha + NI-86/1 EPTC 250 10000 l/ha | 95 | 113 | 0 | 0 |
| 5 EPTC 6 l/ha + NI-86/21 EPTC 250 20000 l/ha | 118 | 113 | 0 | 0 |

EXAMPLE 4

An experiment in cultivating bottle was carried out for comparing the antidoting action of the lyophilized forms of NI-86/21 bacterium with that of NI-86/21 EPTC 250 antidote-carrying bacterium against EPTC, butylate, vernolate and acetochlor, respectively.

1. Material, Equipments and Method 1.1 Preparation of the Lyophilized NI-86/21 and NI-86/21 EPTC 250 Samples A pure NI-86/21 strain culture was inoculated onto slant Nutrient medium (for the composition see Example 2) in 5 glass tubes. After cultivating the bacteria at room temperature for 3 days, the bacterial mass was washed into 5 ml of physiological solution each (see Example 2 for the composition). 0.1 ml of the bacterial suspension each thus prepared was scattered in 100 Petri dishes onto Nutrient plates. After an incubation at 25° C. for 4 days, the bacterium colonies were suspended in 3 ml of physiological solution each which then were carried by tens into 10 Erlenmeyer bottles of 100 ml volume to obtain 10 times 30 ml of bacterial suspension. From these, 3 times 30 ml were treated with 3 times 8 μl of EPTC, then the samples thus obtained were maintained at −10° C. until the lyophilisation carried out on the day 5 after this time point.

The lyophilisation was carried out in a Labor MIM device at −40° C. without using a protective colloid.

On the use of the lyophilized NI-86/21 and NI-86/21 EPTC 250 products were resuspended in 60 ml of tap water each in one bottle, then immediately used simultaneously with the treatments by herbicides preemergently or presowing.

1.2. Cultivating Bottle Experiment

PVC foil-lined plastic bottles with a surface of 0.8 dm$^2$, which were useful for receiving 800 g of soil each, were used for this experiment. First, 400 g of air-dry, upper field soil each were weighed into these bottles. The soil contained 1.95% of humus, had a pH value of 5.7 and a heaviness (according to Arany) of 46.

Onto this soil 10 grains of Pioneer 3901 maize each as well as 20 grains of HIBAR sorghum each were sowed. The sowing was covered by 100 g of soil each, then EPTC in a dose of 6 l/ha, butylate in a dose of 12 l/ha, vernolate in a dose of 6 l/ha and acetochlor in a dose of 3 l/ha, respectively were applied.

Onto the soil surface thus treated, $0.05 \times 10^3$, $0.5 \times 10^3$, $1.0 \times 10^3$ and $2.5 \times 10^3$ l/ha doses, respectively, of the suspension obtained from the lyophilisate of the NI-86/21 bacterial suspension as well as the same doses of the NI-86/21 EPTC 250 biopreparation were separately applied and finally, the soil surface treated was repeatedly covered by 100 g of soil each.

Treatment:
EPTC 6 l/ha
EPTC 6 l/ha + NI-86/21 0.05–0.5–1.0–2.5 × 10$^3$ l/ha
EPTC 6 l/ha + NI-86/21 EPTC 250 0.05–0.5–1.0–2.5 × 10$^3$ l/ha
Butylate 12 l/ha
Butylate 12 l/ha + NI-86/21 0.05–0.5–1.0–2.5 × 10$^3$ l/ha
Butylate 12 l/ha +
NI-86/21 EPTC 250 0.05–0.5–1.0–2.5 × 10$^3$ l/ha
Vernolate 6 l/ha
Vernolate 6 l/ha + NI-86/21 0.05–0.5–1.0–2.5 × 10$^3$ l/ha
Vernolate 6 l/ha +
NI-86/21 EPTC 250 0.05–0.5–1.0–2.5 × 10$^3$ l/ha
Acetochlor 3 l/ha
Acetochlor 3 l/ha + NI-86/21 0.05–0.5–1.0–2.5 × 10$^3$ l/ha
Acetochlor 3 l/ha +
NI-86/21 EPTC 250 0.05–0.5–1.0–2.5 × 10$^3$ l/ha Each treatment was carried out in five repetitions.

The plants were cultivated up to the day 10 after the sowing or after the treatment under HgMIF/400 W daylight lamps, by using a light intensity of 15 KLX, with an illumination period of 16 hours. The water was daily supplemented from above up to the water capacity. The green masses of the plants and the shoot length of the maize were measured. The degree of torsions of the maize was evaluated by using the scale described in Example 1.

2. Results and Conclusions

The results are shown in the Tables VI to XIII. It can be stated from the Tables that the lyophilizate prepared from the NI-86/21 bacteria cultivated on the medium containing 250 ppm of EPTC shows a significant antidoting action. The phytotoxic effect induced in the maize by a 6 l/ha dose of EPTC or 12 l/ha dose of butylate or 6 l/ha of vernolate or 3 l/ha of acetochlor, respectively is eliminated by a 500, 1000 or 2500 l/ha dose of the lyophilizate of NI-86/21 EPTC 250 prepared according to the present invention. Without a pretreatment with EPTC, the NI-86/21 bacterium does not exert any antidoting action.

TABLE VI

The antidoting action of increasing doses of the NI-86/21 bacterial suspension against a 6 l/ha dose of EPTC herbicide in maize

| Dose of EPTC l/ha | NI-86/21 10$^3$ l/ha | Maize Shoot length cm/plant | Green mass g/bottle | Bonitation value |
|---|---|---|---|---|
| 6 | 0 | 4.4 | 2.1 | 4 |
| 6 | 0.05 | 4.8 | 2.8 | 4 |
| 6 | 0.5 | 5.0 | 3.4 | 4 |
| 6 | 1.0 | 5.3 | 3.4 | 4 |
| 6 | 2.5 | 7.6 | 3.9 | 3 |
| Untreated control | | 18.9 | 5.0 | 1 |
| SZD$^{5\%}$ | | 1.7 | 0.8 | |

TABLE VII

The antidoting action of increasing doses of the NI-86/21 EPTC 250 biopreparation against a 6 l/ha dose of EPTC herbicide in maize

| Dose of EPTC l/ha | NI-86/21 EPTC 250 10$^3$ l/ha | Maize Shoot length cm/plant | Green mass g/bottle | Bonitation value |
|---|---|---|---|---|
| 6 | 0 | 4.4 | 2.1 | 4 |
| 6 | 0.05 | 5.9 | 3.1 | 3 |
| 6 | 0.5 | 18.6 | 5.1 | 1 |
| 6 | 1.0 | 20.9 | 5.7 | 1 |
| 6 | 2.5 | 22.5 | 5.8 | 1 |
| Untreated control | | 18.9 | 5.0 | 1 |
| SZD$^{5\%}$ | | 1.7 | 0.8 | |

TABLE VIII

The antidoting action of increasing doses of the NI-86/21 bacterial suspension against a 12 l/ha dose of butylate herbicide in maize

| Dose of butylate l/ha | NI-86/21 10$^3$ l/ha | Maize Shoot length cm/plant | Green mass g/bottle | Bonitation value |
|---|---|---|---|---|
| 12 | 0 | 16.1 | 4.6 | 3 |
| 12 | 0.05 | 16.3 | 4.6 | 3 |
| 12 | 0.5 | 17.4 | 4.8 | 2 |
| 12 | 1.0 | 16.7 | 4.6 | 2 |
| 12 | 2.5 | 15.5 | 4.1 | 2 |
| Untreated control | | 18.9 | 5.0 | 1 |
| SZD$^{5\%}$ | | 1.7 | 0.8 | |

TABLE IX

The antidoting action of increasing doses of the NI-86/21 EPTC 250 biopreparation against a 12 l/ha dose of butylate herbicide in maize

| Dose of butylate l/ha | NI-86/21 EPTC 250 10$^3$ l/ha | Maize Shoot length cm/plant | Green mass g/bottle | Bonitation value |
|---|---|---|---|---|
| 12 | 0 | 16.1 | 5.6 | 3 |
| 12 | 0.05 | 16.0 | 5.0 | 2 |
| 12 | 0.5 | 18.1 | 5.1 | 2 |
| 12 | 1.0 | 18.6 | 5.0 | 1 |
| 12 | 2.5 | 18.7 | 5.0 | 1 |
| Untreated control | | 18.9 | 5.0 | 1 |
| SZD$^{5\%}$ | | 1.7 | 0.8 | |

TABLE X

The antidoting action of increasing doses of the NI-86/21 bacterial suspension against a 6 l/ha dose of vernolate herbicide in maize

| Dose of vernolate l/ha | NI-86/21 10³ l/ha | Maize Shoot length cm/plant | Maize Green mass g/bottle | Bonitation value |
|---|---|---|---|---|
| 6 | 0 | 7.5 | 4.1 | 4 |
| 6 | 0.05 | 6.3 | 3.7 | 4 |
| 6 | 0.5 | 8.1 | 4.0 | 4 |
| 6 | 1.0 | 7.7 | 4.1 | 4 |
| 6 | 2.5 | 12.2 | 4.6 | 3 |
| Untreated control | | 18.9 | 5.0 | 1 |
| $SZD^{5\%}$ | | 1.7 | 0.8 | |

TABLE XI

The antidoting action of increasing doses of the NI-86/21 EPTC 250 biopreparation against a 6 l/ha dose of vernolate herbicide in maize

| Dose of vernolate l/ha | NI-86/21 EPTC 250 10³ l/ha | Maize Shoot length cm/plant | Maize Green mass g/bottle | Bonitation value |
|---|---|---|---|---|
| 6 | 0 | 7.5 | 4.1 | 4 |
| 6 | 0.05 | 8.8 | 4.3 | 4 |
| 6 | 0.5 | 16.6 | 4.6 | 3 |
| 6 | 1.0 | 18.7 | 5.1 | 2 |
| 6 | 2.5 | 19.0 | 5.0 | 1 |
| Untreated control | | 18.9 | 5.0 | 1 |
| $SZD^{5\%}$ | | 1.7 | 0.8 | |

TABLE XII

The antidoting action of increasing doses of the NI-86/21 bacterial suspension against a 3 l/ha dose of acetochlor herbicide in maize

| Dose of acetochlor l/ha | NI-86/21 10³ l/ha | Maize Shoot length cm/plant | Maize Green mass g/bottle | Bonitation value |
|---|---|---|---|---|
| 3 | 0 | 16.0 | 3.9 | 3 |
| 3 | 0.05 | 16.4 | 4.1 | 3 |
| 3 | 0.5 | 16.6 | 4.8 | 2 |
| 3 | 1.0 | 17.3 | 4.8 | 2 |
| 3 | 2.5 | 17.9 | 4.7 | 2 |
| Untreated control | | 18.9 | 5.0 | 1 |
| $SZD^{5\%}$ | | 1.7 | 0.8 | |

TABLE XIII

The antidoting action of increasing doses of the NI-86/21 EPTC 250 biopreparation against a 3 l/ha dose of acetochlor herbicide in maize

| Dose of acetochlor l/ha | NI-86/21 EPTC 250 10³ l/ha | Maize Shoot length cm/plant | Maize Green mass g/bottle | Bonitation value |
|---|---|---|---|---|
| 3 | 0 | 16.0 | 3.9 | 3 |
| 3 | 0.05 | 18.9 | 5.1 | 2 |
| 3 | 0.5 | 19.1 | 5.4 | 1 |
| 3 | 1.0 | 20.8 | 5.5 | 1 |
| 3 | 2.5 | 21.4 | 6.0 | 1 |
| Untreated control | | 18.9 | 5.0 | 1 |
| $SZD^{5\%}$ | | 1.7 | 0.8 | |

EXAMPLE 5

A laboratory experiment was carried out in cultivating bottles in order to investigate the EPTC-antagonizing action in a maize culture of the aqueous and acetone filtrates as well as the residual fibrous substances obtained from the shoot and root of little maize plants preptreated with EPTC.

1. Materials, Equipments and Method 1.1. Preparation of an Antidote-Carrying Maize PVC foil-lined plastic cultivating bottles with a surface of 4 dm² each, which were suitable to receive about 6000 g of air-dry soil each, were used. First, 4000 g of upper field soil each with a humus content of 1.95%, with a pH value of 5.7 and a heaviness (according to Arany) of 46, were weighed into the bottles. Thereon 50 grains of Pioneer 3707 maize each were sowed and covered with 1000 g of soil each. Thereafter, the cultivating bottles labelled by (E) were treated with a 6 l/ha dose of EPTC. The soil surface treated was repeatedly covered by 1000 g of soil each.

The maize plants, which received the treatment (E), were cultivated from the treatment up to the day 14 under HgMIF/400 W daylight lamps with a light intensity of 11 KLX, with a daily illumination period of 16 hours at a temperature of 26°±4° C.

The plants were daily sprinkled from above up to the water capacity. On the day 14, the shoots of the plants were separately cut in each bottle and the roots were washed out of the soil.

1.2 Separation of the Filtrates and the Fibrous Substances from the Maize 1.2.1 The Working Up of the Shoot of Maize Pretreated with EPTC (E)

After the cutting-off, 55 g of the shoot (Ha) of the maize pretreated with EPTC (E) were immediately crushed in 500 ml of water in a turmix machine. The crushing was halved, 250 ml were filtered through a laboratory glass filter and thus an aqueous filtrate (Sz) was obtained therefrom which was labelled by the code E-Ha-Vi-Sz.

The fibrous material remaining on the filter was shaken with 50 ml of acetone in a shaking funnel and the acetone phase was drained off. The acetone phase was labelled by the code E-Ha-Ac-Sz.

The remaining aqueous crushing of 250 ml was filtered through a vacuum filter and the fibrous substance remaining on the filter was taken as a separate sample labelled by the code E-Ha-Vi-R.

1.2.2 The Working Up of the Root of Maize Pretreated with EPTC

The working-up was realized similarly to that described above, except that 28 g of roots crushed by a knife were treated with 400 g of tap water in a turmix machine. The aqueous and then the acetone filtrate were obtained from 200 ml of crushing; the fibrous substance was obtained from the other part of 200 ml volume.

These fractions were labelled by the following codes:
E—Gyö—Vi—Sz
E—Gyö—Vi—R
E—Gyö—Ac—Sz

1.3. The Investigation in Cultivating Bottle of the EPTC-Antagonizing Action of the Filtrates and Fibers Obtained from Maize

1. Arrangement of the Experiment

PVC foil-lined plastic bottles with a surface of 0.8 dm² each were used, which were suitable to receive 800 g of soil each. First, 400 g of upper field soil each having the properties described under 1.1 were weighed into these bottles. Thereon 10 grains of Pioneer 3707 maize each were sowed, the sowing was covered by 100 g of soil each, then EPTC was applied in a dose of 6 l/ha. The soil surface treated and the untreated bottles were repeatedly covered by 100 g of soil each, then 100 ml of the aqueous filtrates each, 100 g of the fibrous material each or 5 ml of the acetone filtrates each, respectively, were applied thereon.

The plants were cultivated under conditions described under 1.1 from the sowing up to the day 7, then the shoot length and green weight of the maize as well as the exterior of the maize were evaluated by using the bonitation scale described in Example 1.

TABLE XIV

The action of the aqueous (Vi) and acetone (Ac) filtrates (Sz) as well as of the residual fibrous substances (R) obtained from the shoot (Ha) of maize pretreated (E) with a 6 l/ha dose of EPTC on the selectivity of EPTC (6 l/ha) herbicide in maize

| Treatment | Maize Shoot length cm/plant | Green mass $10^{-2}$ g/plant | Bonitation value |
|---|---|---|---|
| Untreated control | 19 | 72 | 2.0 |
| EPTC | 9 | 56 | 1.2 |
| EPTC + (E—Ha—Vi—SZ) | 19 | 62 | 1.8 |
| EPTC + (E—Ha—Vi—R) | 19 | 72 | 1.8 |
| EPTC + (E—Ha—Ac—Sz) | 20 | 70 | 2.0 |
| E—Ha—Vi—Sz | 20 | 72 | 2.0 |
| E—Ha—Vi—R | 20 | 79 | 2.0 |
| E—Ha—Ac—Sz | 18 | 68 | 2.0 |

It is obvious from the data of Table XIV that the phytotoxic effect of a 6 l/ha dose of the EPTC herbicide was completely eliminated by the extracts or the residual fibrous material obtained from the shoots of little maize plants pretreated with a 6 l/ha dose of EPTC. As a result of the antidoting action of these biopreparations, the shoot length and exterior of the cultivated plant remained intact and healthy, similar to those of the untreated control.

TABLE XV

The action of the aqueous (Vi) and acetone (Ac) filtrates (Sz) as well as of the residual substances (R) obtained from the root (Gyö) of maize pretreated (E) with a 6 l/ha dose of EPTC on the selectivity of EPTC (6 l/ha) herbicide in maize

| Treatment | Maize Shoot length cm/plant | Green mass $10^{-2}$ g/plant | Bonitation value |
|---|---|---|---|
| Untreated control | 19 | 72 | 2.0 |
| EPTC | 9 | 56 | 1.2 |
| EPTC + (E—Gyö—Vi—Sz) | 5 | 16 | 1.0 |
| EPTC + (E—Gyö—Vi—R) | 19 | 72 | 2.0 |
| EPTC + (E—Gyö—Ac—Sz) | 18 | 70 | 2.0 |
| E—Gyö—Vi—Sz | 7 | 22 | 1.4 |
| E—Gyö—Vi—R | 20 | 73 | 2.0 |
| E—Gyö—Ac—Sz | 19 | 68 | 2.0 |

It is a quite obvious from the data of Table XV that both the acetone filtrate as well as the residual fibrous material obtained from the root of little maize plants pretreated with a 6 l/ha dose of EPTC show an excellent antidoting action.

We claim:

1. A process for the preparation of an antidote-carrying Pioneer 3707 maize plant part, which is useful for lowering the cultivated plant damaging effect of the thiolcarbamates of the Formula (I)

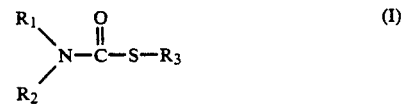

wherein $R_1$ and $R_2$ are the same or different, and stand for $C_{1-6}$alkyl or $C_{3-6}$cycloalkyl group, or $R_1$ and $R_2$ together with the nitrogen atom, to which they are attached, form a hexamethylenimino group; and $R_3$ means a $C_{1-5}$alkyl group, or chloroacetanilides of the Formula (VIII),

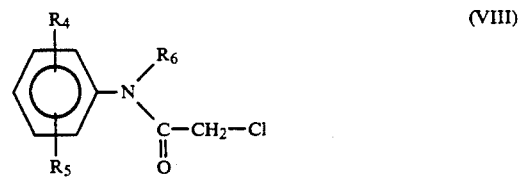

wherein $R_4$ and $R_5$ are the same or different and stand for hydrogen or $C_{1-5}$alkyl group; and $R_6$ means a $C_{1-5}$alkyl, $C_{2-5}$alkenyl, $(C_{1-3}$alkoxy)-$(C_{1-3}$alkyl) or pyrazolyl-$(C_{1-3}$alkyl) group, which comprises the steps of:

(a) cultivating Pioneer 3707 maize seeds in field soil or under laboratory conditions to obtain cultivated maize plants;

(b) applying to the Pioneer 3707 maize seeds cultivated during step (a) a compound of the Formula (I)

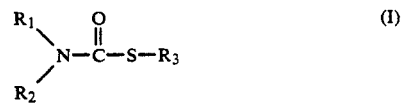

or an acylated or esterified derivative thereof so as to obtain maize plants carrying a herbicidal antidote wherein the herbicidal antidote is a maize-protective amount of a compound of the Formula (II) through (VII)

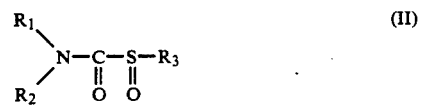

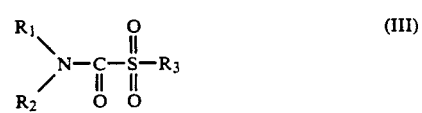

-continued

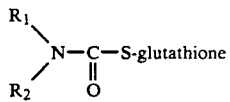
(IV)

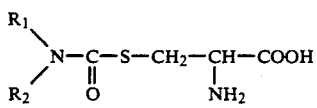
(V)

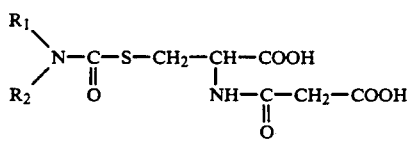
(VI)

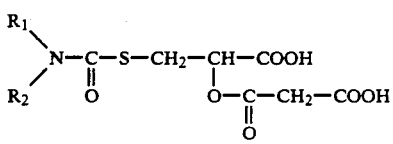
(VII)

or a mixture thereof or an acylated or esterified derivative thereof;

(c) harvesting the Pioneer 3707 maize plants carrying a herbicidal antidote within 30 days following the application of the compound of the Formula (I);

(d) isolating the root or shoot portions of the Pioneer 3707 maize plant harvested according to step (c), crushing said root or shoot portions in water and filtering the crushed root or shoot portions in the water to obtain a filtrate and a fibrous material on the filter; and (e) recovering either the filtrate or the fibrous material obtained from the maize shoot or recovering the fibrous material obtained from the maize root to obtain an antidote-containing maize plant part.

2. The process defined in claim 1 wherein according to step (b) the compound applied to the cultured Pioneer 3707 maize seeds is a compound of the Formula (I).

3. The process defined in claim 2 wherein the compound of the Formula (I) applied to the cultured Pioneer 3707 maize seeds is EPTC.

* * * * *